United States Patent
Fillmore et al.

(10) Patent No.: US 7,361,506 B2
(45) Date of Patent: Apr. 22, 2008

(54) DIFFERENTIATION OF SPECIALIZED DERMAL AND EPIDERMAL CELLS INTO NEURONAL CELLS

(75) Inventors: Helen Fillmore, Richmond, VA (US); Shelley Hoover, Richmond, VA (US); William C. Broaddus, Midlothian, VA (US); George Gillies, Charlottesville, VA (US)

(73) Assignee: Creative Science Solutions, Inc., Richmond, VA (US)

( * ) Notice: Subject to any disclaimer, the term of this patent is extended or adjusted under 35 U.S.C. 154(b) by 107 days.

(21) Appl. No.: 11/022,805

(22) Filed: Dec. 28, 2004

(65) Prior Publication Data

US 2005/0158286 A1    Jul. 21, 2005

Related U.S. Application Data

(62) Division of application No. 10/147,925, filed on May 20, 2002, now abandoned.

(60) Provisional application No. 60/292,176, filed on May 18, 2001.

(51) Int. Cl.
*C12N 5/00* (2006.01)
*C12N 5/02* (2006.01)
*C12N 5/08* (2006.01)

(52) U.S. Cl. .................. 435/371; 435/373; 435/377; 435/383

(58) Field of Classification Search ............... 435/373, 435/377, 384, 371, 383
See application file for complete search history.

(56) References Cited

FOREIGN PATENT DOCUMENTS

WO    WO 97/23602    *   7/1999

OTHER PUBLICATIONS

Zhang et al., "An enhanced green fluorescent protein allows sensitive detection of gene transfer in mammlian cells", Biochemical and Biophysical Research Communications, 227, 707-711 (1996), article No. 1573.*

* cited by examiner

*Primary Examiner*—Ruth A Davis
(74) *Attorney, Agent, or Firm*—Whitham Curtis Christofferson & Cook, PC

(57) ABSTRACT

Cells are generated from skin biopsies for use in cell implantation by identifying a source of skin cells that have a surface concentration of at least one cell selected from the group consisting of keritinocytes and/or melanocytes; taking a sample of tissue from the surface area; mechanically disaggregating the tissue samples; collecting the disaggregated cells; washing the disaggregated cells; filtering the washed disaggregated cells; providing a cell suspension with filtered and washed keritinocytes and/or melanocytes; and suspending the cell suspension in a medium. In greater particularity, the method may comprise a) identifying a source of skin cells that have a surface concentration of at least 400 cells per square millimeter of surface area of at least one cell selected from the group consisting of keritinocytes and/or melanocytes; b) taking a sample of those skin cells and culturing them to enrich for cells selected from the group consisting of keritinocytes and melanocytes to form cultured cells for transplantation purposes c) concentrating the cells selected from the group consisting of keritinocytes and/or melanocytes from the cultured mass of cells; and d) differentiating the concentrated cells selected from the group consisting of keritinocytes an/or melanocytes.

3 Claims, 4 Drawing Sheets

DIFFERENTIATION OF SPECIALIZED DERMAL AND EPIDERMAL CELLS INTO NEURONAL CELLS

This application is a divisional of pending U.S. patent application 10/147,925, filed May 20, 2002 now abandoned, which claims benifit of U.S. provisional application 60/292,176, filed May 18, 2001 the complete contents of which arehereby incorporated by reference.

BACKGROUND OF THE INVENTION

1. Field of the Invention

The present invention relates to the field of cellular biology, particularly to the field of cell implantation therapy, more particularly to the development of a source of cells that may be used directly or for the cloning of cells for use in cell implantation therapy, and more particularly to the in vivo dedifferentiation of certain skin cells as implantable cells for the production of cells for transplantation or implantation cell therapies.

2. Background of the Art

Cell implantation requires significant levels of control in the introduction of cells. The cells must be capable of performing the specific functional replacement or addition therapy desired in the transplantation or implantation, and the cells must be compatible with the receiving organism. Present techniques emphasize the use of same species differentiated cells or the use of compatible undifferentiated cells for use in the implantation therapy. Conservative protocol has generally motivated investigators to prefer same species undifferentiated cells or specialized same species differentiated cells for use in such procedures. This considered preference has limited the source of cells that can be used for implantation therapy. For example, viable, mature, differentiated cells are not readily available, and the moral implications of fetal tissue collection of undifferentiated cells has limited the sources of such cells, as well as the natural quantity limitation on the source itself.

Cell implantation using tissue-derived nuclear transfer embryos has been performed, with attendant nuclei replacement to provide the targeted specialty cells for implantation. Bovine skin fibroblast cells were transferred into enucleated bovine oocytes, resulting in a fetus. The ventral mesoncephalon was isolated from the bovine fetus. When transplanted, this tissue successfully ameliorated symptoms in the Parkonsonian rat (Zawada et al., 1998, Nature Medicine, 4:569-574). Skin fibroblast cells from cows, sheep, pigs, monkeys, and rats have been used as sources of donor nuclei, as well as nuclei from human sources.

The clinical management of numerous neurological disorders has been frustrated by the progressive nature of degenerative, traumatic or destructive neurological diseases and the limited efficacy and the serious side-effects of available pharmacological agents. Because many such diseases involve destruction of specific "neuronal clusters" or brain regions, it has been hoped that grafting of neural cells or neuron-like cells directly into the affected brain region might provide therapeutic benefit. Cell transplant approaches have taken on a major emphasis in current Parkinson's disease research, and may prove useful in promoting recovery from other debilitating diseases of the nervous system including Huntington's disease, Alzheimer's disease, severe seizure disorders including epilepsy, familial dysautonomia, as well as injury or trauma to the nervous system. In addition, the characterization of factors which influence neurotransmitter phenotypic expression in cells placed into the brain may lead to a better understanding of normal processes and indicate means by which birth defects resulting from aberrant phenotypic expression can be therapeutically prevented or corrected. Neurons or neuronal-like cells can be grafted into the central nervous system (CNS), in particular, into the brain, either as solid tissue blocks or as dispersed cells. However, to date, a number of problems of both a technical and ethical nature have plagued the development of clinically feasible grafting procedures.

Parkinson's disease results from a selective loss of dopaminergic nigrostriatal neurons, resulting in a loss of input from the substantia nigra to the striatum. Solid grafts of tissues potentially capable of producing dopamine, such as adult adrenal medulla and embryonic substantia nigra (SN), have been used extensively for experimental grafting in rats and primates treated with 6-hydroxydopamine (6-OHDA) to destroy dopaminergic cells (Dunnett, S. B. et al., Brain Res. 215: 147-161 (1981); ibid. 229: 457-470 (1981); Morisha, J. M. et al., Exp. Neurol. 84: 643-654 (1984); Perlow, M. J. et al., Science 204: 643-647 (1979)). Grafts of embryonic SN have also been used as therapy for primates lesioned with the neurotoxin 1-methyl-4-phenyl-1,2,3,4-tetrahydropyridine (MPTP), which produces a Parkinson's-like disease (Redmond, D. E. et al., Lancet 8490: 112-27 (1986)).

The methods of the present invention are useful for treating a number of human neurological disease. Parkinson's Disease can be treated according to the present invention by implanting dopamine-producing cells in the recipient's striatum. Alzheimer's disease involves a deficit in cholinergic cells in the nucleus basalis. Thus, according to the invention, a subject having Alzheimer's disease or at risk therefore may be implanted with cells producing acetylcholine.

Huntington's disease involves a gross wasting of the head of the caudate nucleus and putamen, usually accompanied by moderate disease of the gyrus. A subject suffering from Huntington's disease can be treated by implanting cells producing the neurotransmitters gamma amino butyric acid (GABA), acetylcholine, or a mixture thereof. According to the present invention, the support matrix material to which such cells are attached is preferably implanted into the caudate and putamen.

Epilepsy is not truly a single disease but rather is a symptom produced by an underlying abnormality. One skilled in the art will appreciate that each epileptic subject will have damage or epileptic foci which are unique for the individual. Such foci can be localized using a combination of diagnostic methods well-known in the art, including electroencephalography, computerized axial tomography and magnetic resonance imaging. A patient suffering from epilepsy can be treated according to the present invention by implanting the support matrix material to which GABA-producing cells are attached into the affected site. Since blockers of glutamate receptors and NMDA receptors in the brain have been used to control experimental epilepsy, cells producing molecules which block excitatory amino acid pathways may be used according to the invention. Thus implantation of cells which have been modified as described herein to produce polyamines, such as spermidine, in larger than normal quantities may be useful for treating epilepsy.

The methods of the present invention are intended for use with any mammal that may experience the beneficial effects of the methods of the invention. Foremost among such mammals are humans, although the invention is not intended to be so limited, and is also applicable to veterinary uses.

Thus, while the feasibility of the transplant approach has been established experimentally, this approach is severely limited by the need for the use of fetal tissue or specifically differentiated cells from the same organ of the organism, which is of limited availability and potentially of great political consequence. In essence, transplantation of human fetal tissue from aborted pregnancies has been prohibitive in the United States. It would thus be of great benefit if simple, routine and safe methods for the successful transplantation of socially acceptable and available tissue into the brain were available for the treatment of debilitating neurological disease.

One potential approach to this problem has been the implantation of adult cells, attempted by Aebischer and his colleagues, who have successfully implanted into the brain selectively permeable biocompatible polymer capsules encapsulating fragments of neural tissue which appeared to survive in this environment (Aebischer, P. et al., Brain Res. 448: 364-368 (1988); Winn, S. R. et al., J. Biomed Mater Res. 23: 31-44 (1989). The polymer capsules, consisting of a permselective polyvinyl chloride acrylic copolymer XM-50, completely prevented the invasion of the encapsulated tissue by host cells. Based on the permeability, antibodies and viruses would be expected to be excluded as well. When dopamine-releasing polymer rods were encapsulated into such a permselective polymer and implanted into denervated striatum in rats, alleviation of experimentally-induced Parkinson disease symptoms was achieved (Winn S. R. et al., Exp. Neurol. 105: 244-50 (1989). Furthermore, U.S. Pat. No. 4,892,538 (Aebischer et al., issued Jan. 9, 1990) discloses a cell culture device for implantation in a subject for delivery of a neurotransmitter comprising secreting cells within a semipermeable membrane that permits diffusion of the neurotransmitter while excluding viruses, antibodies and other detrimental agents present in the external environment. The semipermeable membrane is of an acrylic copolymer, polyvinylidene fluoride, polyurethane, polyalginate, cellulose acetal, polysulphone, polyvinyl alcohol, polyacrylonitrile, or their derivatives or mixtures and permits diffusion of solute of up to 50 kD molecular weight. This device was said to be useful in treatment of neurotransmitter-deficient conditions, such as Parkinson's disease, by sustained, local delivery of neurotransmitters, precursors, agonists, fragments, etc., to a target area, especially the brain. The device may be made retrievable so that the contents may be renewed or supplemented, and the cells are protected against immunological response and viral infection.

By the term "neural or paraneural origin" is intended a cell which is derived from the embryonic neural crest. A preferred example of a cell of paraneural origin is an adrenal medullary chromaffin cell. The precursor cells to the mammalian adrenal medulla are of neural crest origin and possess the potential to develop along either neuronal or endocrine lines of differentiation (Bohn, M. C. et al., 1981, supra, Devel. Biol. 89: 299-308 (1982); Unsicker, K., Develop. Biol. 108: 259-268 (1985)). Chromaffin cells from the rat, monkey, and human adrenal medulla, when removed from adrenal cortical influences and exposed to nerve growth factor (NGF), change from an endocrine to a neuronal phenotype (Notter, M. F. et al., Cell Tiss. Res. 244: 69-70 (1986); Stromberg, I. et al., Exp. Brain Res. 60: 335-349 (1985); Unsicker, K. et al., 1978, supra). When co-grafted with cerebral cortical or hippocampal tissue into the anterior chamber of the rat eye, adrenal chromaffin cells form nerve fibers which innervate the adjacent co-grafted brain tissue (Olson, L. A. et al., Exp. Neurol. 70414-426 (1980)).

Another paraneural cell type is a retinal pigment epithelium cell (Song, M-K et al., J. Cell. Physiol. 148: 196-203 (1990)).

U.S. Pat. No. 5,958,767 discloses that clones of human NSCs (neural stem cells)—unambiguously affirmed by the presence of a common retroviral insertion site and propagated by either epigenetic or genetic means—can participate in normal CNS development in vivo and respond to normal microenvironmental cues, including migration from various germinal zones along well-established migratory routes to widely disseminated regions. A single NSC is capable of giving rise to progeny in all 3 fundamental neural lineages—neurons (of various types), oligodendroglia, and astroglia (hence, multipotency)—as well as giving rise to new NSCs with similar potential (i.e., self-renewal). In vivo, following transplantation into mouse hosts, a given human NSC clone is sufficiently plastic to differentiate into neural cells of region- and developmental stage-appropriate lineages along the length of the neural axis: into neurons where neurogenesis normally persists, and into glia where gliogenesis predominates, emulating patterns well-established for endogenous murine progenitors, with which they intermingle seamlessly. Thus, for example, they will give rise to neurons following migration into the Olfactory Bulb (OB) at one end of the neuraxis and into granule neurons in the cerebellum at the other, yet also yield astroglia and oligodendroglia, the appropriate cell types born in the postnatal neocortex, subcortical white matter, and striatum. Of additional significance, as might be expected of a true stem cell, many of the neuronal types into which these NSCs could differentiate, are born not at the developmental stage from which the cells were initially obtained (e.g. midgestation), but rather at the stage and region of NSC implantation, thus affirming appropriate temporal (in addition to regional) developmental responsiveness.

Neural stem cells were thought to have limited differentiation capabilities within the species. However, adult mouse NSC were transferred into early mouse and chick embryos and contributed to all three germ layers in the developing mouse and chick embryo. This demonstrated that these particular NSC cells were capable of differentiating into multiple cell types (Clarke et al., 2000 Science vol 288: 1660). The mechanism was not stated to be effective for other than the chosen organisms, there was no specific mechanism described such as transdifferentiaion or mutation, and there was no indication that determined cells could actually reverse their direction of differentiating and differentiate in a different direction in human neural stems cells, which are quite advanced compared to the cells selected in this analysis.

Stenevi et al. (Brain Res. 114: 1-20 (1976) found that the best results were obtained with fetal CNS neurons which were placed next to a rich vascular supply. In fact, a review of the literature reveals that tissue from almost every area of the fetal brain can be successfully transplanted if care is taken with procedural details (see, for example, Olson, L. A. et al., In: Neural Transplants: Development and Function, Sladek, J. R. et al., eds,. Plenum Press. New York, 1984, pp. 125-165).

Embryonic tissue provides an excellent source of cells that will differentiate in a foreign environment and become integrated with the host tissue. For example, grafts of embryonic SN into 6-OHDA treated rats have been shown to produce dopamine, to reduce apomorphine- or amphetamine-induced rotation, to alleviate sensory deficits and to make synapses in the host striatum (Dunnett et al., Morisha et al., Perlow et al., supra). Grafted neurons are also spontaneously active, thus mimicking normal adult SN neurons (Wuerthele, S. M. et al., In: Catecholamines, Part B, (E. Usdin et al., eds.), A. R. Liss, Inc., New York, pp. 333-341).

In contrast to successful grafting of fetal neural tissue, mature CNS neurons have never been found to survive in transplants (Stenevi, U. et al., Brain Res. 114: 1-20 (1976)). The reason fetal CNS neurons survive grafting procedures, while adult neurons do not is uncertain, but probably related to several factors. First, fetal neurons are less affected by low oxygen levels than mature neurons (Jilek, L., In: Developmental Neurobiology, Himwich, W. A., ed., C. C. Thomas Publisher, Springfield, Ill., 1970, pp. 331-369), and grafting procedures necessarily involve periods of anoxia until an adequate blood supply to the transplant is established. Secondly, fetal neurons seem to survive best when they are taken during a rapid growth phase and before connections are established with target tissues (Boer, G. J. et al., Neuroscience 15: 1087-1109, (1985)). Also, fetal tissue may be especially responsive to growth (or "survival") factors that are known to be present in the milieu of the damaged host brain (Nieto-Sampedro, M. et al., Science 217: 860-861 (1982); Proc. Natl. Acad. Sci. USA 81: 6250-6254 (1984)).

In further human studies (Lieberman, supra; Lindvall, O., J. Neurol. Neurosurg. Psychiat., 1989, Special Supplement, pp. 39-54; Bakay, R. A. E., Neurosurg. Clin. N. Amer. 1: 881-895 (1990)), autologous grafts have been attempted to replace the need for fetal material. In this procedure the patients first underwent initial abdominal surgery for the removal of a healthy adrenal gland. The patient then was subjected to similar neurosurgery as that for the fetal adrenal transplant. The surgical morbidity-mortality for the combined adrenalectomy/neurosurgery was expectedly high. The ultimate therapeutic result was claimed to be as high as 30% but may have been as low as one patient in the series of six. There was no evidence that the adrenal material transplanted into these patients survived.

However, despite the promise of fetal tissue and cell transplants, the art has turned to alternate sources of donor tissues for transplantation because of the ethical, moral, and legal problems attendant to utilizing fetal tissue in human medicine. These sources include neural and paraneural cells from organ donors and cultured cell lines. (See, for example: Gash, D. M. et al., In: Neural Grafting in the Mammalian CNS, Bjorklund, A. et al., eds, Elsevier, Amsterdam, 1985, pp. 595-603; Gash, D. M. et al., Science 233: 1420-22 (1986)).

There are suggestions in the literature that there may be an additional advantage of grafting dissociated cells compared to blocks of tissue in that the cells can be precultured with various substances such as growth factors prior to grafting or they can be co-grafted with other cells or substances which promote specific parameters of differentiation. Furthermore, glial cells may have specific regional effects and produce neuronal growth factors (Barbin, G. et al., Devel. Neurosci. 7: 296-307 (1985); Schurch-Rathgeb, Y. et al., Nature 273: 308-309 (1978); Unsicker, K. et al. Proc. Natl. Acad. Sci. USA 81: 2242-2246 (1984); Whitaker-Azmitia, P. M. et al., Brain Res. 497: 80-85 (1989)). This suggests that co-transplanting cells providing the desired neurotransmitters along with specific types of glia that produce glial-derived factors, may promote neuronal growth and the desired differentiation of grafted cells.

Although early clinical experiments using the grafting approach did not result in long-lasting effects, an initial report of one study appeared more promising (Madrazo et al., Soc. Neurosci. Abstr. 12: 563 (1986); for an overview, see: Lieberman, A. et al., Adv. Tech. Stand. Neurosurg. 17: 65-76 (1990), which is hereby incorporated by reference). However, the surgical procedure used required craniotomy or full "open brain" surgery in which a portion of healthy striatum was removed and replaced with "chunks" of fetal adrenal gland. The therapeutic results obtained were somewhat controversial. However, both the need for serious neurosurgery in an already debilitated population and the need to use fetal tissue makes this approach undesirable.

Transdetermination has been observed in lower orders such as *Drosophila*, where a sample of cultured imaginal cells sometime differentiate into a structure appropriate to an imaginal disc other than that from which the culture was derived. Transdetermination represent a switch from one heritable state to another and so resembles the consequence of genetic mutation. (see Bruce Alberts, et al., Molecular Biology of the Cell, 1983, Garland Publishing Co., New York, N.Y., Ch. 15, pages 838-839). This phenomenon has been reported as occurring with groups of cells, but with cells of both the mutant and normal genotypes present.

Neural progenitor/stem cells obtained from fetal tissue or non-human tissue have been shown to be effective for cell replacement therapy for neurodegenerative disorders, head trauma, stroke and spinal cord injuries, and have been extrapolated to predict similar efficacy in repair of any type of nerve cell or brain cell damage. It has been recently found that neural progenitor/stem cells exist in the adult human brain, and that when these cells are cultured, the cells repeatedly divide and can (under the appropriate influences well defined in the art) differentiate into neurons, astorcytes and oligodendroglia.

In addition, PCT application WO 98/07841 discloses that one human cross species embryo was produced using human oral cavity epithelium as the donor nucleus. One NT unit developed to what was asserted to be a blastocyst stage embryo. This was placed on a feeder layer of cells. A cell mass appeared on the plate. However, there was no report of any information to suggest that the cell line was of human origin.

U.S. Pat. No. 6,087,168 (Levesque et al.) describes a method of converting, or transdifferentiating the epidermal cells into viable neurons useful in both cell therapy and gene therapy treatment methodologies. The method of transdifferentiating epidermal cells into neuronal cells comprises the following steps: obtaining skin cells from a patient; dedifferentiating these cells with an appropriate medium, neurotrophin or cytokine; transfecting the skin cells with one or more expression vector(s) encoding at least one neurogenic transcription factor or active fragments thereof, expressing at least one of the neurogenic transcription factors; growing the transfected cells in an appropriate medium; and adding to the medium one or more antisense oligonucleotide(s) corresponding to at least one negative regulator of neuronal differentiation, whereby the epidermal cells are transdifferentiated into neuronal cells. The Experimental Basis of that Invention is described as a transdifferentiation process involving the following basic steps of:

1. Isolation of proliferating epidermal basal cells from the skin of a patient in need;

2. Dedifferentiation of epidermal basal cells in calcium free growth media;

3. Expression of neurogenic basic-Helix-Loop-Helix (NeuroD1, NeuroD2, ASH1) and/or Zn-finger (Zic3, MyT1) transcription factors with simultaneous suppression of the expression of homeobox genes MSX1 and bHLH transcription factor HES1 in epidermal basal cells; and 4. Growing cells resulting from step 3 (cells which over-express neurogenic transcription factors and have suppressed expression of MXS1 and HES1) in the presence of low concentrations of all-trans retinoic acid and various neurotrophins, such as, BDNF, NGF, NT-3, and NT-4.

In the first step of that invention, epidermal or skin cells are obtained from a patient in need. These epidermal cells are obtained or isolated via any type of surgical procedure. Preferably, these isolated cells are epidermal basal cells obtained from the skin of a patient. However, epithelial, or any other type of basal cell or proliferating cell population, can be used for the conversion of these cells into neurons.

In the second step of that process, preferentially epidermal basal cells are dedifferentiated in a calcium free growth medium. This step involves treatment of the cells obtained in step one so that the cells lose the majority of differentiation specific gene expression to become dedifferentiated, that is, more primitive or developmentally less advanced. The dedifferentiation process is significant in that it allows for reprogramming of the neuronal development pathway. Since calcium ions are required to support development of keratinocytes (skin cells) from basal cells, removal of calcium results in dedifferentiation of basal cells. In other proliferating cell types, however, calcium may not be necessary to support development of any particular developmental pathway that is being deregulated. Other means to achieve the desired end of dedifferentiation involve treating the cells with specific growth factor or cytokines. Also, altering the specific gene expression pathway that is responsible for differentiation of epidermal cells by genetic manipulation may be used instead of eliminating calcium in the growth media. Moreover, elimination of calcium may not be required if other than proliferating epidermal basal cells are used.

In the third step, the process of that invention utilizes molecular manipulation techniques to alter the cell differentiation pathway of epidermal cells. This alteration is accomplished by allowing for the expression of neurogenic transcription factors, such as the basic-Helix-Loop-Helix factors, Neuro D1, Neuro D2, or ASH1, and/or zinc-finger transcription factors, such as Zic3 or MyT1, while simultaneously, or near simultaneously, suppressing the expression of genes responsible for suppression of the neuronal development pathway, such as the basic-Helix-Loop-Helix factor HES1 and/or the homeobox factor MSX1. In addition to these genes, any other set of neurogenic and anti-neurogenic genes can be manipulated so as to achieve the desired end of transdifferentiation of epidermal cells or other proliferating cell types. Manipulations that can be used in this step of the inventive process include the use of variety of gene transfer protocols, such as microinjection of expression constructs, and a variety of DNA transfection techniques (such as, lipofections, liposomes, coprecipitation techniques, and different carriers), and viruses. Also protein transfer methods can be used to transiently express neurogenic transcription factors in the proliferating dediffernentiated cells. Finally, in the fourth step of that invention, the transdifferentiated cells are preferably grown in the presence of a retinoid, such as all trans retinoic acid or vitamin A derivatives. In addition, neurotrophins or cytokines, such as BDNF, NGF, NT-3, NT-4, IL-6, can be used to obtain a substantial population of transdifferentiated neuronal cells. This step is optional in that it is not required for transdifferentiation. However, treatment with a retinoid and at least one neurotrophin increases the number of cells obtained.

SUMMARY

A method for generating cells from skin biopsies for use in cell implantation comprises: identifying a source of skin cells that have a surface concentration of at least one cell selected from the group consisting of keritinocytes and/or melanocytes; taking a sample of tissue from the surface area; mechanically disaggregating the tissue samples; collecting the disaggregated cells; washing the disaggregated cells; filtering the washed disaggregated cells; providing a cell suspension with filtered and washed keritinocytes or melanocytes; and suspending the cell suspension in a medium. In greater particularity, the method may comprise a) identifying a source of skin cells that have a surface concentration of at least 400 cells per square millimeter of surface area of at least one cell selected from the group consisting of keritinocytes and melanocytes; b) taking a sample of those skin cells and culturing them to increase the surface concentration of cells selected from the group consisting of keritinocytes and/or melanocytes to form a cultured mass of cells; c) concentrating the cells selected from the group consisting of keritinocytes and melanocytes from the cultured mass of cells; and d) differentiating the concentrated cells selected from the group consisting of keritinocytes and melanocytes. The differentiated cells may then be implanted into a patient. A preferred surface concentration of melanocytes is at least 500, at least 700, and at least 800 melanocytes per square millimeter of skin. A preferred surface concentration of keritinocytes is at least 500 keritinocytes per square millimeter of skin, or at least 700 keritinocytes per square millimeter. The method may use a medium in which the cell suspension is suspended comprises a nutritional medium. Such a nutritional medium may, for example, be selected from the group consisting of DMEM/F12+N2 supplement, bFGF, EGF containing less than 10% fetal calf serum, and Melanocyte basal medium.

DETAILED DESCRIPTION OF THE INVENTION

Figure 1A:
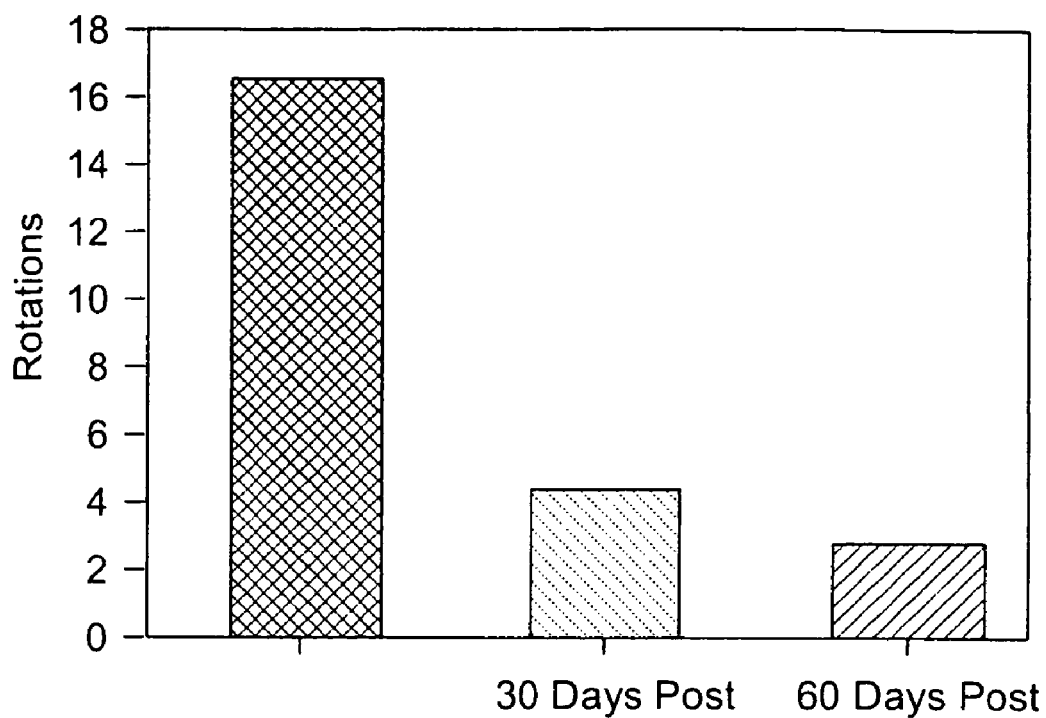
FIG. 1A-F. Transplantation of melanocytes into 6-OHDA lesioned rats. Intracranial injection of 6-OHDA into the substantia nigra is a well characterized model for Parkinson's Disease. It is well known that rats with lesions treated with amphetamine will display circling behavior that can be measured in rotations. In the controls FIGS. 1E and F), the rats were lesioned with 6-OHDA, however there were no cells transplanted. Rats that have no lesion and when treated with amphetamine will not circle (data not shown). In experimental rats (FIG. 1A-D), melanocytes were injected into the substantia nigra using sterotactic coordinates. Note the differences in scale of the six figures.
Figure 1B:
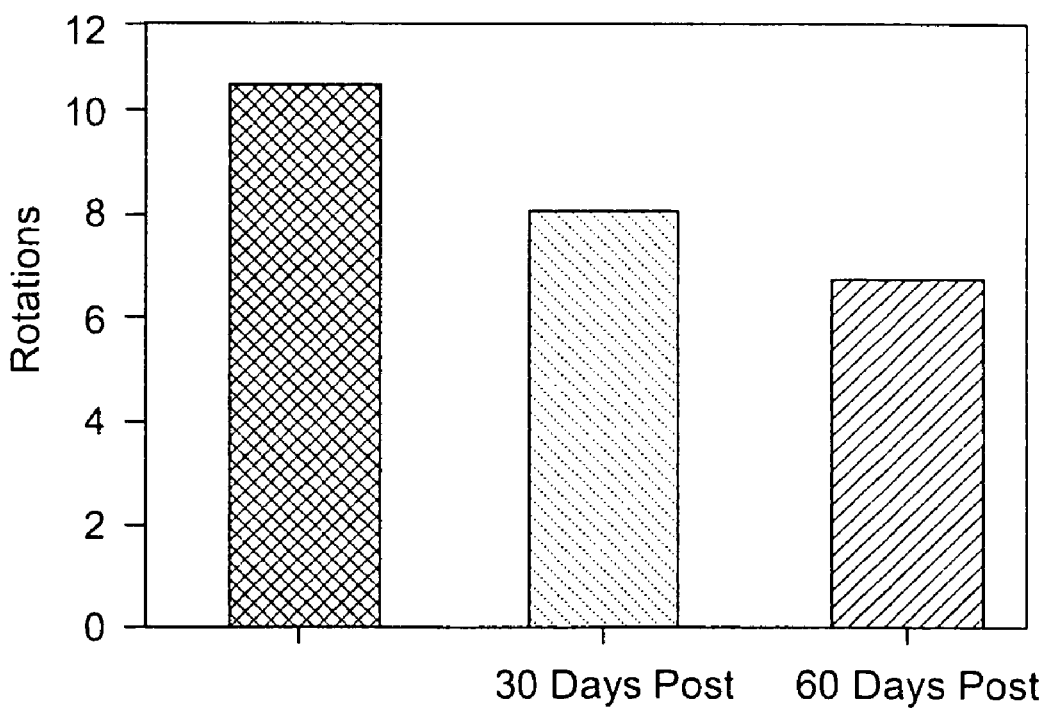
Figure 1C:
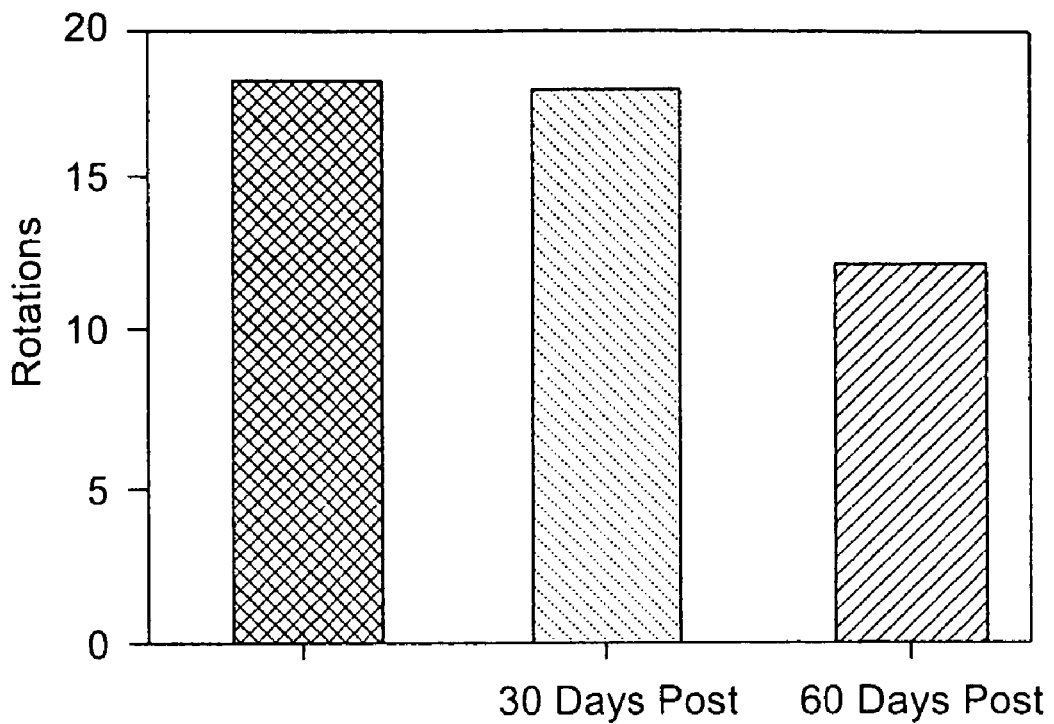
Figure 1D:
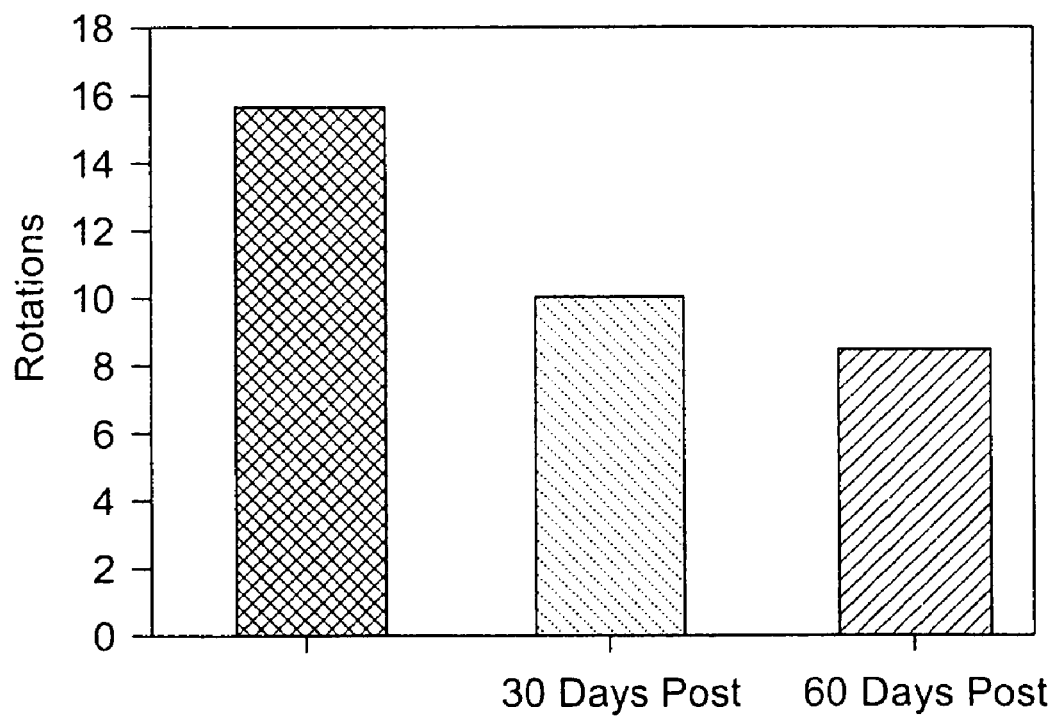
Figure 1E:
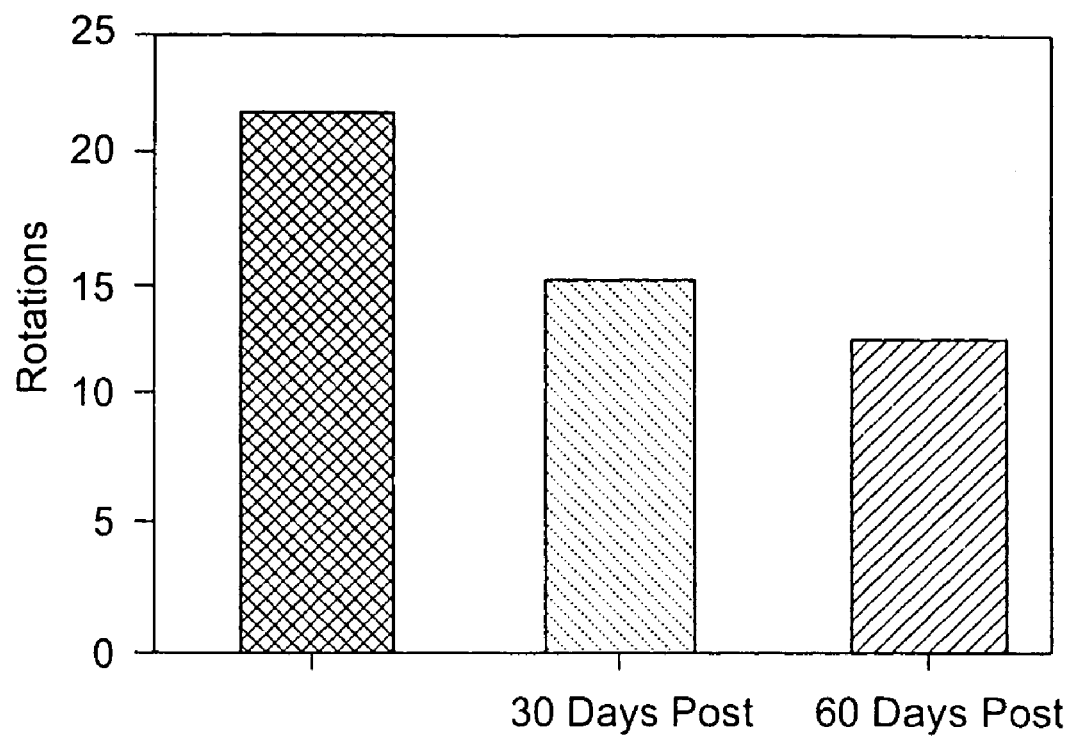
Figure 1F:
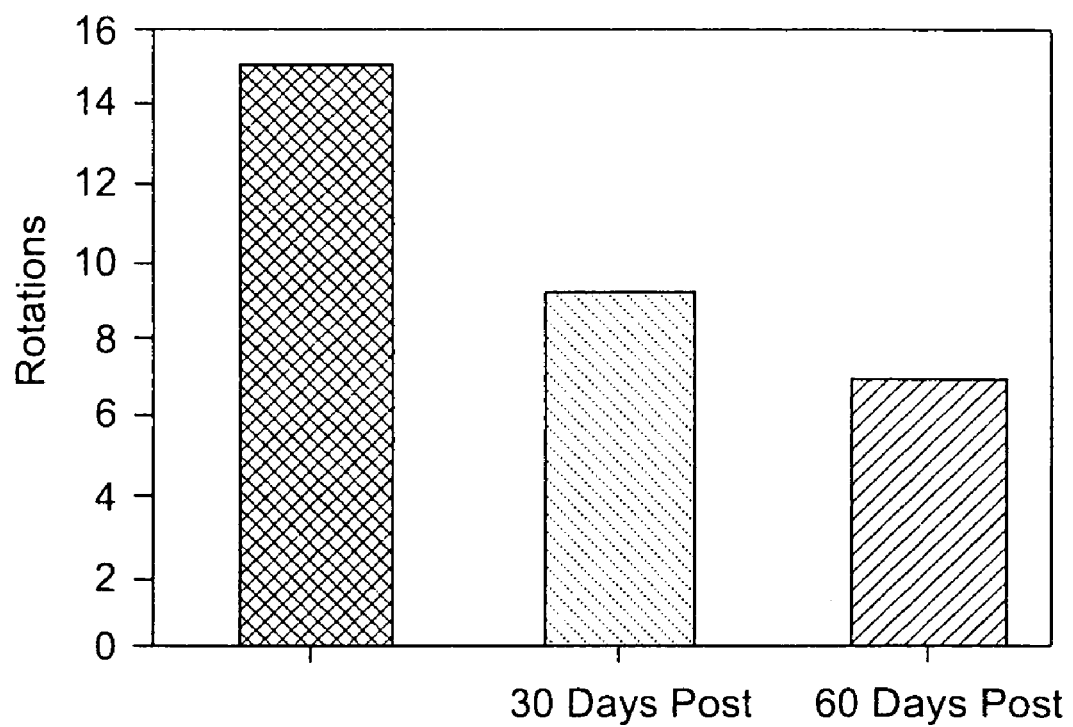

Two specific types of cells that can be sourced from skin biopsies have been identified as providing the potential for enhanced capability in the generation of adult stem cells. In particular, melanocytes and pericytes have been identified as being capable of being differentiated into other cells when exposed to appropriate differentiating factors. These cells may be collected from regions of their naturally high concentration in the skin by biopsy and/or concentrated from biopsies taken with more moderate levels of these particular cells being present. By selecting, focusing upon, and concentrating cells that predominate with melanocytes and pericytes, a large source of cells is provided for efficient differentiation into specific cell types.

To appreciate this invention, the difference between the selection of source cells used in the practice of the present invention and the source of cells used by Levesque (U.S. Pat. No. 6,087,168) should be appreciated. Levesque takes a complete biopsy of a dermis. The biopsy includes only epidermis cells, and then selects only epidermal basal cells for further differentiation. Levesque shows that basal cells will differentiate into transient amplification cells, including keritinocytes. Any type of proliferating cells can be used according to Levesque. That reference, in fact, uses a whole garnish of cells in the original biopsy sampling, and doesn't distinguish among the cells in the practice of the invention.

In the present invention, biopsies rich in melanocytes and pericytes are used. Fetal foreskin is a particularly rich source of these cells. It is also feasible to isolate these classes of cells from an adult, with or without procedures to concentrate these cells from the sample. The pericytes and melanocytes would then be differentiated in their rich sample, preferably with different approaches for each type of cell (i.e., using different differentiating procedures and materials).

One particularly desirable method for providing these cells is to collect a sample that has a modest or relatively rich content of these cells and then to increase that specific type of cell from source. For example, a melanocyte is not an epidermal basal cell, but is a transient cell derived from a neural crest cell. During embryonic development they develop along the spine. The original rich source of the cells may be obtained by first seeking an initial source (e.g., by using cell surface markers to separate them).

The present invention comprises a process of generating cells from skin biopsies for use in cell implantation comprising:

a) identifying a source of skin cells that have a surface concentration of at least 400 cells per square millimeter of surface area of at least one cell selected from the group consisting of keritinocytes and melanocytes;

b) taking a sample of those skin cells and culturing them to increase the surface concentration of cells selected from the group consisting of keritinocytes and melanocytes to form a cultured mass of cells; and c) concentrating the cells selected from the group consisting of keritinocytes and melanocytes from the cultured mass of cells;

d) differentiating the concentrated cells selected from the group consisting of keritinocytes and melanocytes.

The method may then have the differentiated cells implanted into a patient. The method may select the identified cells to comprise melanocytes or keritinocytes. The surface area concentration of the cells may be, for example, at least 500 cells (e.g., melanocytes) per square millimeter of skin, at least 700 melanocytes per square millimeter of skin, or at least 800 melanocytes per square millimeter of skin.

Information on Melanocytes

Melanocytes, which are derived from the neural crest, are localized in the retinal pigment epithelium (RPE) and uveal tract of the eye, the leptomeninges, mucous membranes, hair matrix, skin dermal-epidermal interface, and dermis. In the skin and hair follicles, the melanoctyes are considered secretory melanocytes (as opposed to continent melanocytes) and in the skin the melanocytes are located in the basal layer and project dendrites into the malpighian layer of the epidermis. The number of melanocytes varies depending on location and range between 1000-2000 cells per square millimeter (Table 1.) Melanocytes located in the RPE (these are derived from optic cup not neural crest), mucous membrane, and leptomeninges are considered continent melanocytes. The distinction between secretory and continent pertains to the synthesis and release of melanin pigments.

The present invention arose in part from an investigation of the effects of LIF on cells of the neural crest. The neural crest is a population of precursor cells that arises from the dorsal lip of the neural tube during embryogenesis and migrates through the embryo along a complex series of pathways. After migration, the crest cells give rise to a great variety of cell types including the neurons and Schwann cells of the sensory and autonomic ganglia, the enteric nervous system, adrenal medulla, melanocytes of the skin and facial mesenchyme. When studied at the population level, the crest appears to be a multipotent collection of stem cells. The extensive transplantation experiments of Le Douarin and colleagues, whereby quail neural crest were grafted into chick embryos, showed that the developmental fate of the crest cells was determined by the location of this graft in the chick embryo. This not only indicated that the full developmental repertoire of the crest is contained in the different subpopulations of grafted crest cells, but also that environmental factors play a major role in the final differentiated phenotype of the cells.

In the last decade it has become increasingly clear that the neural crest contains subpopulations of cells that are already committed to particular developmental pathways (2. Ziller, C., Fauquet, M., Kalcheim, C., Smith, J., & Le Douarin, N. M. Dev. Biol. 120: 101-111, 1987; Anderson, D. J. Neuron 3: 1-12, 1989).

A number of soluble trophic factors have been shown to act as survival agents for neural crest derived neurons, but none of these have been shown to act directly on the neuronal precursor cells within the neural crest. These factors include nerve growth factor (NGF; Levi-Montalcini, R. Annu. Rev. Neurosci. 5: 341-362, 1982).

However, it is also clear that the differentiation of these cells is determined by environmental factors, such as brain-derived neurotrophic factor (BDNF; Barde, Y. Neuron. 2: 1525-1534, 1989), and ciliary neurotrophic factor (CNTF; Barbin, G., Manthorpe, M., & Varon, S. J. Neurochem. 43: 1468-1478, 1984) and the fibroblast growth factors (FGF's; see Barde, supra).

Levesque describes the use of "epidermal basal cells" in the practice of that invention. This is a very broad category of cells and does not distinguish among the many available types of cells. The specific cell types that Levesque selects are within the basal layer. Basal cells are themselves derived from pericytes, and as transient amplifying cells become keratinocytes. Levesque, in fact, suggests they are trying to get rid of keratinocytes and then differentiate the residue (the basal cells) second generation cells from original stem cells.

Epidermal stem/Pericytes are cells that are often described as being located at the bottom of hills on the juncture of cells, at the junction between the dermis and epidermis. Upon removal of biopsies rich in pericytes, according to the invention one would then amplify the concentration of pericytes. Germinative/stem cells are located mostly in the stratum basalis but also at the tips of epidermal rete ridges. The epidermal stem/pericytes have low metabolic activity. Sourcing of melanocytes could be done by taking a biopsy of normal skin and amplifying the melanocytes or taking out a mole (nevus) with melanocytes that are in the dermis and or epidermis (e.g., neva). One may remove the basal cells by panning them out to concentrate the melanocytes. This is in stark contrast to Levesque. Antibodies, cell surface antibodies, binding agents, may be used to conjugate the targeted cells to assist in their initial concentration from suspensions. Epidermal stem/Pericytes may be treated in the same way to concentrate them. This tends to provide a mass of cells that approaches foreskin model in quality. This rich supply of conjugated cells may then be separated from the different skin cells in the mass.

The conjunctiva is the tissue that lines the eyelids, and covers the anterior portion of the globe of the eye (except for the cornea). The conjunctiva consists of a delicate membrane composed of an epithelium, and a substantia propria, that overlie the tough outer portion of the eyeball known as the sclera. The epithelium is stratified into multiple cell layers, and provides a barrier to the penetration of compounds into the eye. There are desmosomal junctions connecting the epithelial cells to one another, and tight junctions between the surface cells that prevent the penetration of small ions. Other cells that can be found in the normal conjunctival epithelium include: goblet cells, which are specialized cells that secrete mucin; Langerhans cells; melanocytes; a small population of immune cells (lymphocytes and neutrophils); and an interspersed neuronal component. Beneath the epithelium, the substantia propria contains stromal cells interspersed in a layer of connective tissue. The substantia propria also contains a microvasculature, lymphatics, immune cells, and neurons. Mast cells are not found in the normal conjunctival epithelium, but tissue type mast cells reside in the substantia propria. The conjunctiva responds to eye irritants by mounting an inflammatory response. The conjunctival response is assessed in the Draize rabbit eye test as redness, chemosis, and discharge.

It is also of significance to note as another distinguishinging feature from Levesque, that even though that reference selects a mass (dermis) with a large number of different types of cells, melanocytes are not technically included included as cells that originate in the dermis. Rather, they migrate to that locations and therefore only incidentally reside at this site (both in the epidermal layer and the dermal layer).

Levesque also refers to dedifferentiating cells by supplying the cells with molecular factors for transdifferentiation. Again, this is a broad and general statement. In fact, it appears that the process supplies the cells with molecular factors for transdifferentiation, which may properly be considered to acting on the cells with transfection methods on their cDNA constructs. Therefore, it appears that in that portion of the text, Levesque is using a large amount of a chemical to block certain genes and insert certain genes for genetic expression. Levesque is adding desired genes and blocking others that exist in the cells. It is also not clear what resultant cell types are in the exemplified process of Levesque, even in specific examples. For example, in Example I, it isn't clearly apparent as to what cells are being obtained.

Collection and propagation/culturing of cells in the practice of the present invention can be described in fairly general terms that are supported by common practices in the field that are tailored to the practice of the present invention. First, previous work with skin keritinocytes in tissue culture suggested that cells with stem cell-like characteristics were enriched in cell culture when grown in conditions that induced premature terminal differentiation (Rogers et al., J. Cell Biol. 110: 1767-1777, 1990; Parkinson et al., Carcinogenesis 3, 525-531, 1982). Second, retinoic acid (RA) has been demonstrated to be an effective differentiating agent in embryonal stem cells in tissue culture (Humes and Cielinski, supra; Rogers et al., supra). Third, Epidermal Growth Factors (EGF) is potent (Humes et al., Lab Invest. 64: 538-545, 1991; Parkinson, supra). Thus, the combination of a potent growth promoter, EGF, and a differentiating agent, RA, would provide positive selection pressure for cells which have a high capacity for replication and negative selection pressure for cells which are terminally differentiating. Although serial passage of specifically differentiated cells from skin cells have been difficult to achieve previously, these growth conditions with RA and EGF are examples of conditions than can result in an ability to grow these cells. The use of both RA and EGF are desirable for consistent passage of these cells. The ability of these particular classes of epidermal cells to morphologically differentiate and form into the desirable cell structures can be easily demonstrated in primary culture followed by growth under selection pressure with RA and EGF for several passages. Resultant cells grown under this selection condition can then be dispersed to prepare a single cell preparation, suspended in three-dimensional collagen gels and grown in serum-free, hormonally defined culture media supplemented with RA and EGF for 7 to 14 days (suitable procedure are described in Yang et al., Proc. Natl. Acad. Sci. U.S.A., 76: 3401-3405, 1979; Bennett, Nature 285: 657-659, 1980; Montesano et al., Cell 42: 469-477, 1985, the texts of which are incorporated herein by reference). Within several days, cells grown under these conditions in collagen gels form luminal tubular structures as evidenced by phase contrast microscopy. Progressive passage of cells promoted increasingly more defined structures. Semi-thin sections of the collagen preparation can confirm the nature of the cell clusters. In either EGF, RA, or both EGF and RA in combination are omitted from the culture media, structures within the collagen gel are not as likely to form in satisfactory quantities. Thus, both EGF and RA may be present in the growth media for preferred methods of cultivation of cells to form into the appropriate phenotype in vitro.

A filtration device may be used to concentrate either the source cells and/or the resultant cells. Such a device has been used for purifying blood and suitably comprises either a single semipermeable hollow fiber or a collection of semipermeable hollow fibers in which are coated, either externally or internally, with a layer of extracellular matrix (ECM) upon which either may or may not be grown a confluent monolayer of epithelial and/or endothelial cells. Alternatively, the cells or matrix may be incorporated directly within or on the polymeric structure of the semipermeable hollow fiber during manufacture.

A filtration device promotes ultrafiltration of blood via convective transport of water and solutes out of the blood or supporting liquid and across the wall of a semipermeable hollow fiber with high hydraulic permeability. Filtration of blood by a convective process has several distinct advantages: it imitates the glomerular process of toxin removal with increased clearance of higher molecular weight solutes and removes all solutes up to a selected molecular weight cutoff at the same rate. Convective transport occurs independently of the existing concentration gradient and depends predominantly on the hydraulic pressure gradient across the membrane.

With respect to the use of a de-differentiating process/procedure followed by differentiation, those of skill in the art will recognize that is not absolutely necessary to genetically modify the makeup of cells used in implantation. The addition of certain growth factors can also be used, so that the expression of genes is changed but not the genetic makeup of cells, as is the case when transfecting DNA is utilized. For example, different growth factors may be added, e.g., growth factors that differentiate cells into dopaminergic neuron cells. In this manner, one may take melanocytes, culture them, grow them, and replace them. A first general process involves harvesting or collecting determined but not differentiated donor cells from an organism, and then growing the collected cells by either maturing the cell, propagating the cell, culturing the cell, or implanting the cell. This characterization of determination versus differentiation is measured or detected by an ability to detect differentiated cells or determined cells in vitro via membrane surface markers, different gene expression patterns and/or morphological markers. Previous teachings emphasizes collection and the direct implantation of determined but not differentiated cells in vivo to assert dedifferentiation followed by targeted differentiation. Alternatively, the determined but not differentiated cells may be placed into an in vitro environment with a differentiating environment established by the presence of differentiating cells and/or differentiating factors present in the in vitro environment, with subsequent implantation.

Almost any cell implantation procedure sourcing in vitro generated or propagated cells and tissue must use a cell growth technique. Cell growth can be performed, for example, according to the known techniques of U.S. Pat. Nos. 5,945,577 and 5,096,822, which are incorporated herein by reference for this applicable disclosure.

In a preferred embodiment, the donor cells are provided from a human source. The process is carried out by propagating the donor cell in appropriate media or directly introducing the determined but not differentiated cells into a host and inducing dedifferentiation and/or differentiation into an implantable cell for the target species. In the case of providing cells for neural cell therapy, it is most desirable to select cells that are already determined but not differentiated towards the appropriate neural cell or select other determined but undifferentiated cell that will differentiate within the in vivo host implantation environment or by in vitro propagation of the cell in an environment that has been stocked with the appropriate differentiating factors.

The cells from the species from which the cells are collected may be chosen from among any determined but undifferentiated cell, such as being selected from germ cells or stem cells, such as primordial germ cells, oogonia, neural stem cells, trophoblast, slightly differentiated embryonic stem cells (primitive ectoderm) or other less determined but still undifferentiated cells. The selected determined but not differentiated, cells act substantially the same as native young, differentiating but undifferentiated cells that can flourish in the growth to harvesting stage (or maturation stage in vivo). The fact that these essentially 'whole' differentiated implantable cells are grown from determined but undifferentiated plastic cells (whether in vitro or in vivo) and then implanted, assures that local differentiating factors at the implantation site will assure or at least assist their proper growth to the desired functionality. This practice is substantially different from the common practices today, where essentially undetermined cells from living organisms are grown in vitro in the presence of selected differentiation factors. That method may use both or either local and natural differentiating factors to direct the functional growth of the collected cells.

Material and Methods for the Isolation of Melanocytes and Skin Stem Cell/Pericytes.

In the performance of a biopsy, it is necessary to discuss risk/benefits and obtain patient consent. The area must be cleaned (e.g., with betadine solution) to create a sterile environment. A local anesthesia may be given (injection of 1% lidocaine with epinephrine). The surgeon would then take a 4 mm punch biopsy obtained by cutting through the epidermis and dermis subcutaneous tissue. The punched sample of tissue is placed in a betadine solution for transport to the laboratory. The lesioned area is closed with a 4-0 nylon suture. It is then typical to apply a topical antibiotic and wound dressing, following written and verbal instructions on wound care. Sutures are removed 10-14 days following biopsy. Tissue dissociation and preparation of single cell suspension follows.

In the present application, by "genetic manipulation of the cells" we mean any means of adding or inhibiting gene expression in the cells e.g. the addition of new genetic material by DNA transfection, viral transduction, anti-sense RNA addition, etc. Examples include but are not limited to: insertion of a gene encoding the enzyme responsible for dopamine synthesis (tyrosine hydroxylase); and inhibition of tyrosinase by the addition of anti-sense RNA or DNA. By "the use of growth factors and/or inhibitors" we mean the addition of those factors either during culturing of the cells or after transplantation of the cells into a host. Alternatively, such factors may be added to the cells (or to their environment) at both of those junctures. Inhibitors may be either chemical (e.g. a chemical inhibitor of tyrosinase) or genetic (as described above).

In particular, when the cells are melanocytes, it may be preferable to both inhibit one precess while stimulating another, e.g. inhibiting tyrosinase and inducing tyrosine hydroxylase expression, the end result being the production of dopamine.

The following examples are to be considered as exemplary of various aspects of the present invention and are no intended to be limiting with respect to the practice of the invention. Those of ordinary skill in the art will appreciate that alternative materials, conditions, and procedures may be varied and remain within the skill of the ordinarily skilled artisan without departing from the general scope of the invention as taught in the specification.

EXAMPLES

Example One

This example relates to a method for obtaining single cell suspensions from human tissue from biopsy tissue. Single cell suspensions are obtained from the skin and or nevus by conventional punch or other surgical means. Single cell suspensions can be prepared from biopsy either by chemical or mechanical dissociation techniques which are standard techniques known in the field. Single cell suspensions were prepared using the DAKO Medimachine™ and accessories (Carpinteria, Calif.). For each tissue sample, the tissues were placed on a pre-wetted medicon (paper) filter and inserted into the Medimachine™ to mechanically disaggregate the tissue samples for 30 seconds to 1 min. Following the collection of dissociated cells, the medicon filter was washed with 1 ml ice-cold PBS and run through the Medimachine™ once again. Following the second collection, the cells were combined and pipetted (ten times) using a glass pipette and then filtered twice over a filcon filter (30 micrometer, DAKO). Separate and sterile medicon filters and filcon filters were used for each sample. The cell suspension was centrifuged and washed with ice-cold PBS, centrifuged again, then resuspended in media. The media is either DMEM/F12+N2 supplement, bFGF, EGF (20 ng) containing no or 10% fetal calf serum or Melanocyte basal medium and supplements purchased from Clonetics (Bio-Whittaker Inc.).

Growth factors that were used or could be used include, but are not limited to, the protein family members of, Interlukein 1, CNTF, PDGF, NT, retinoic acid, NGF, scatter factor, BMP, GDNF, LIF, and Nurr. In addition, in some cases the cells will be incubated with human neurons hTN in the presence or absence of substrate.

Example Two

This prophetic example shows the potential use of cells for the stable transfection of the tyrosine hydroxylase gene and the dopa decarboxylase gene under an inducible promoter. The tyrosine hydroxylase gene and other genes that would act as co-factors for the synthesis of dopamine would be cloned into inducible systems. The inducible systems could include, but are not limited to the tetracycline inducible system, or an irradiation inducible system. The inducible systems can be genetically engineered to be activated with the addition of drug, stimulus or removal of drug or stimulus. The tyrosine hydroxylase gene and other genes which could act as co-factors for the synthesis of dopamine would be inserted into the collected cells. According to procedures understood in the art, the cells would be rendered into a tetracycline inducible system, an irradiation inducible system or other inducible system.

Example Three

This prophetic example anticipates the use of cells for the inhibition of the tyrosinase gene and protein product by either genetic engineering of an antisense DNA construct or the use of chemical inhibition or growth factor inhibition.

Example Four

Another prophetic use of the cells would be for the induction of dopa decarboxylase protein expression by growth factor stimulation.

Example Five

Another prophetic use of cells would be for the stable transfection of the EGFP gene and the EGFP gene co-expressed with other genes of interest for the visualization of cells in vivo. TA marker gene would also be subcloned into an inducible system including the tetracycline, irradiation or MR induced construct. The cells stably transfected with a marker gene under the control of for example an MRI inducible system would allow for the detection of cells transplant into host tissue.

Example Six

This prophetic example shows the potential use of these cells to immunopurify specific cell types by using antibodies such as c-Kit (CD117) conjugated to superparamagnetic (magnetic only in a magnetic field) microparticles (sized in the micron range) that are synthesized by polymerizing polystyrene or polyacrolein in the presence of a magnetite ferrofluid or by formation of an agglomerate by silanation of a ferrofluid. With both of these preparations antibodies can be covalently coupled by the resultant surface character of the particles. Magnetic microparticles have been used in cell separation, immunoassays, isolation, identification and genetic analysis of specific nucleic acid sequences, and for isolation of DNA binding proteins. The present inventors have examined the possibility of using similar magnetic microparticles as a solid support for immunoabsorption of intact plastids from whole cell lysates because their relatively high magnetic moment allows ease of separation using simple rare earth magnets. Another class of particle preparations can be described as magnetic nanoparticles (ferrofluid derivatives sized in the nanometer range) consisting of ferric oxide crystals encapsulated by dextran (Molday, R., Yen, S., and Rembaum, A., slowly in conventional ferromagnetic fields. Consequently, organelles labeled with magnetic nanoparticles must be separated in a magnetic affinity column (Miltenyi et al., supra). Disclosed herein is the use of antibodies specific to exposed epitopes of proteins on chloroplast outer envelopes coupled to magnetic nanoparticles to immuno-isolate various plastid subtypes from whole cell lysates.

Table 1. This Table provides information upon which the present invention is based, with the document source content of the number of melanocytes per millimeter square skin has been reported. Numbers are taken from Jimbow et al., (1993) and represent a median age of 16-92 years. The number of melanocytes per millimeter square decrease with increasing age. The idea place for skin pericytes is the fetal foreskin.

| Location | Numbers of melanocytes/mm$^2$ |
| --- | --- |
| Scalp | 1025-1060 |
| Face | 1010-1194 |
| Neck | 920-926 |
| Chest | 687-918 |
| Arm | 717-908 |
| Back | 865-880 |
| Abdomen | 578-605 |
| Buttock | 405-565 |
| Genitalia | 1047-1228 |
| Thigh | 771-917 |
| Lower Leg | 812-814 |

Reference Biology of Melanocytes. Jimbow K., Quevedo W C., Fitzpatrick T B., and Szabo G. (1993) pp 261-289. In Dermatology in General Medicine Vol I. 4th edition. Eds. Fitzpatrick, T. B., Eisen, A. Z., Wolff K., Freedberg, I. M., Austen K. F. McGraw-Hill Inc. New York.

Example Seven

This prophetic example shows the potential use of cells for transplantation. An example is demonstrated in FIGS. 1 and 2. According to procedures understood in the art, the cells (melanocytes, keritinocytes, or pericytes) would be transplanted into CNS tissue and monitored for de-differentiation either without growth factor or genetic manipulation or with growth factor and genetic manipulation.

EXAMPLE EIGHT

Figure 2A:
FIGS. 2A and B. Tyrosine hydroxylase positive immunohistochemistry of 6-OHDA lesioned rats transplanted with melanocytes. Arrows indicate tyrosine hydroxylase positive cells. Control lesioned rats not transplanted with melanocytes do not show positive cells (data not shown).
Figure 2B:

As seen in FIGS. 1-2, melanocytes were implanted into the brain of 6-OHDA rats. Those skilled in the art will recognize this well-characterized Parkinson's Disease model. In this example, melanocytes were transplanted without genetic or growth factor manipulation to determine if the environment or "niche" can influence de-differentiation. In two of the experimental animals (FIG. A and B) rotational behavior was improved suggesting an effect of cell transplantation. (Note the difference in scale of the various figures). To determine if the transplantation survived and de-differentiated into dopamine producing cells, immunohistochemistry was conducted as described in FIG. 2.

What is claimed:

1. A method for generating cells for use in cell implantation comprising:
   a) identifying a source of skin cells that have a surface concentration of at least 400 cells per square millimeter of surface area, wherein said skin cells include melanocytes;
   b) taking a sample of said skin cells;
   c) culturing said sample to increase the surface concentration of melanocytes to form a cultured mass of cells;
   d) concentrating the melanocytes from the cultured mass of cells; and
   e) implanting said melanocytes into an environment that induces de-differentiation of said melanocytes into cells that produce tyrosine hydroxylase.

2. The method of claim 1 further comprising a step of concentrating said melanocytes prior to said step of culturing.

3. The method of claim 1 wherein said source of skin cells is selected from the group consisting of skin biopsy tissue, mole biopsy tissue, and fetal foreskin.

* * * * *